United States Patent [19]

Smith, III

[11] Patent Number: 5,085,210
[45] Date of Patent: Feb. 4, 1992

[54] SLEEVE FOR MAINTAINING POSITION OF ORTHOPEDIC KNEE BRACE

[76] Inventor: Kirby Smith, III, 2942 Cheshire Dr., Marietta, Ga. 30062

[21] Appl. No.: 594,766

[22] Filed: Oct. 9, 1990

[51] Int. Cl.$^5$ .............................................. A61F 5/00
[52] U.S. Cl. ....................................... 602/26; 602/63
[58] Field of Search ................. 128/80 R, 80 C, 80 F, 128/88, 165

[56] References Cited

U.S. PATENT DOCUMENTS

| | | | |
|---|---|---|---|
| 2,877,033 | 3/1959 | Koetke | 128/80 F X |
| 3,710,790 | 1/1973 | Lemon | 128/165 |
| 3,970,081 | 7/1976 | Applegate, Jr. | 128/165 X |
| 4,097,932 | 7/1978 | Lacey | 128/80 F X |
| 4,296,744 | 10/1981 | Palumbo | 128/165 X |
| 4,323,059 | 4/1982 | Rambert et al. | 128/80 C |
| 4,366,813 | 1/1983 | Nelson | 128/80 C |
| 4,370,978 | 2/1983 | Palumbo | 128/165 X |
| 4,476,857 | 10/1984 | Levine | 128/165 X |
| 4,513,740 | 4/1985 | Westlake | 128/165 |
| 4,685,278 | 8/1987 | Mitsuoka | 128/165 X |
| 4,686,969 | 8/1987 | Scott | 128/80 C |
| 4,726,362 | 2/1988 | Nelson | 128/165 X |
| 4,751,920 | 6/1988 | Mauldin et al. | 128/80 F X |
| 4,765,318 | 8/1988 | Tranberg et al. | 128/165 X |
| 4,832,010 | 5/1988 | Lerman | 128/165 |
| 4,953,543 | 9/1990 | Grim et al. | 128/80 F X |

FOREIGN PATENT DOCUMENTS 8604811 8/1986 World Int. Prop. O. .......... 128/165

Primary Examiner—Richard J. Apley
Assistant Examiner—Linda Dvorak
Attorney, Agent, or Firm—Caesar, Rivise, Bernstein, Cohen & Pokotilow, Ltd.

[57] ABSTRACT

A sleeve to hold an orthopedic knee brace in place on the knee of a person. The sleeve is elastic, e.g., neoprene, to enable it to be stretched to encircle the person's calf, and has a top end, an inner surface, an outer surface. A strap is secured to the top end of the sleeve. A brace mount is secured on the outer surface of the sleeve. The inner surface of the sleeve is resistant to sliding on the skin of the person when the sleeve is in place on the person's calf. The strap has an elongated free end portion arranged to be wrapped around at least a portion of the sleeve adjacent the top end and to be releasably secured in that position, whereupon the inside diameter of the portion of the sleeve underlying the strap is confined to a diameter which is less than the diameter of the widest portion of the wearer's calf so that the sleeve is precluded from slipping down the calf. The brace mount comprises either a Velcro (TM) component, fixedly secured to the sleeve and arranged to be releasably secured to a cooperating Velcro component fixedly secured on the first portion of the brace or a pocket into which the first portion of the brace is disposed.

25 Claims, 4 Drawing Sheets

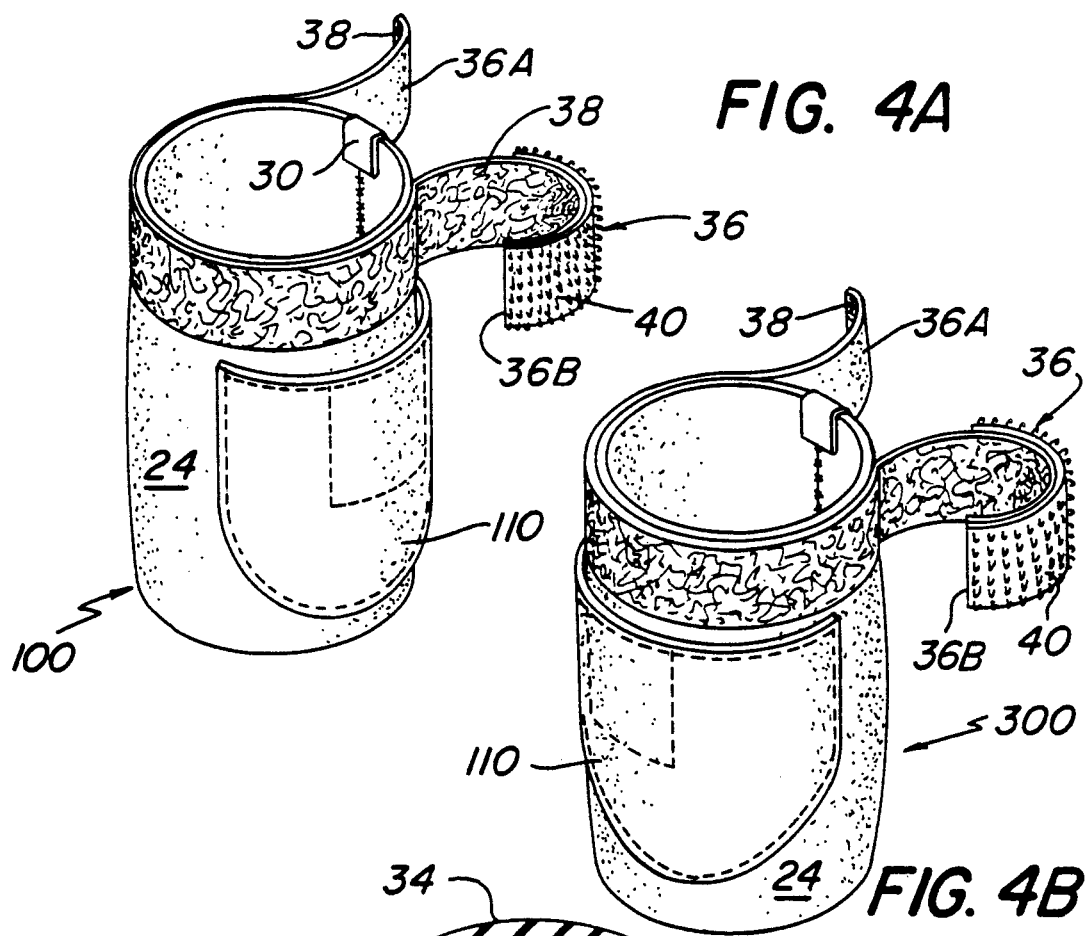
FIG. 4A
FIG. 4B
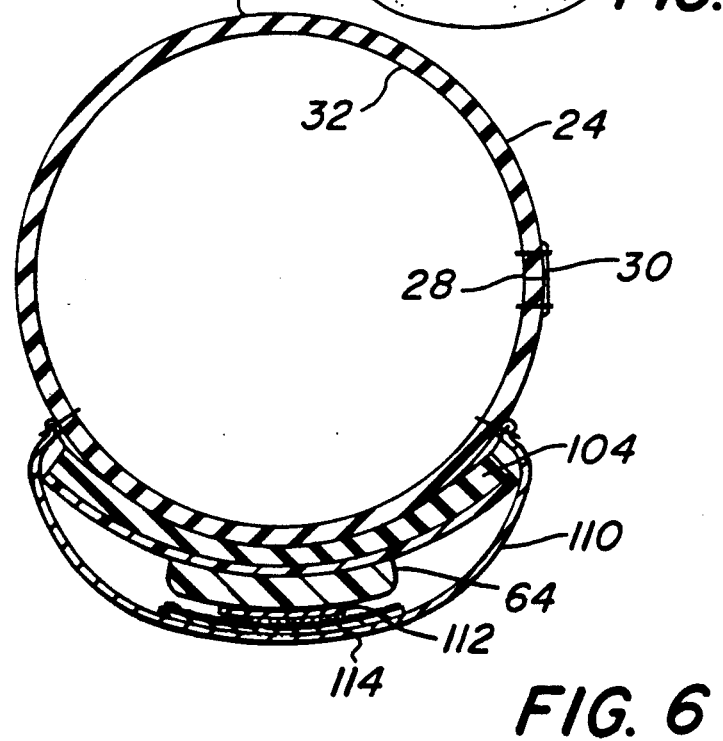
FIG. 6

SLEEVE FOR MAINTAINING POSITION OF ORTHOPEDIC KNEE BRACE

This invention relates generally to orthopedic knee braces, and more particularly to sleeves for use therewith to maintain the position of an orthopedic knee brace on the knee of a person.

BACKGROUND OF THE INVENTION

Various types of knee braces are shown in the patent literature and are commercially available. Examples of such prior art braces are shown in the following U.S. Pat. No.: 4,370,977 (Mauldin et al), 4,372,298 (Lerman), 4,407,276 (Bledsoe), 4,481,941 (Rolfes), 4,487,200 (Feanny et al), 4,493,316 (Reed et al), 4,503,846 (Martin), 4,541,515 (Nishimura et al), 4,628,916 (Lerman et al.) and 4,715,363 (Detty). Examples of prior art knee braces which are commercially available are the following: the PRO-tector, PRO 24, and P.A.R. knee braces sold by Pro Orthopedic Devices, Inc. of Tucson, AZ, the ANDERSON KNEE STABLER protective knee brace sold by Omni Scientific, Inc of Martinez CA, the MCDAVID KNEEGUARD knee brace sold by McDavid Co. of Clarendon Hills, IL., the CTi brace sold by Innovation Sports, Inc. of Irvine, CA, the DONJOY FOUR-POINT brace sold by Donjoy, Inc. of Carlsbad, CA, and the LENNOX HILL brace sold by Lenox Hill Brace Co. of Long Island City, NY.

Many of the foregoing braces, while suitable for their intended purposes, nevertheless suffer from a common problem, namely, they tend to migrate or slip down the leg when in use. Such action causes an inconvenience and potential problem for the wearer of the brace. In this regard the wearer must stop his/her activity to reposition the brace. Moreover, while the brace is out of position the wearer loses the maximum benefit of the support that the brace was designed to provide. Indeed, the brace may move so far out of position as to put the wearer in danger of injury.

As will be appreciated by those skilled in the art no matter how well designed or fitted a brace may be, it has to overcome two main obstacles to remain in position. The first obstacle is gravity, since it poses an unrelenting force pulling the brace down. The second obstacle is the constant expansion and contraction of the wearer's muscle tissue as the wearer moves about.

With the foregoing in mind manufacturers of knee braces have tried a variety of means to maintain proper brace position. In this regard many braces incorporate what can be called a "calf strap", which is a non-elastic strap coming across the top of the calf and cinching down tightly in the hope that it will not slide down over the largest part (sometimes called the "belly") of the calf. Another approach has been to use a cloth or neoprene under-sleeve, that is, a thin sleeve covering the leg under the entire length of the brace. This is done in the hope of providing a more frictionally engaging surface to the wearer's skin so that the brace will hold in position and not slip. In fact most commercially available braces are lined with some form of "non-slip" material, e.g., neoprene, nylon, etc. Unfortunately the foregoing approaches have not completely eliminated the migration or slipping problem. Even the lateral prophylactic braces which are now so popular in football exhibit migration or slipping problems, notwithstanding the variety of strapping techniques used thereby. In fact, short of using some adhesive, e.g., adhesive tape, nothing heretofore has seemed to eliminate the problem.

OBJECTS OF THE INVENTION

Accordingly, it is the general object of this invention to provide a sleeve which overcomes the disadvantages of the prior art.

It is a further object of this invention to provide a sleeve for use with an orthopedic knee brace for securely holding the knee brace in position on the user's knee.

It is another object of this invention to provide a sleeve for use with various types of commercially available orthopedic knee braces for securely holding any of such braces in position on the user's knee.

It is still a further object of this invention to provide a sleeve which is readily securable to the calf of a user to securely mount a knee brace on the user's knee against slippage.

It is yet a further object of this invention to provide a sleeve which is simple in construction and relatively low in cost.

SUMMARY OF THE INVENTION

These and other objects of the instant invention are achieved by providing a sleeve to hold an orthopedic knee brace in place on the knee of a person. The brace includes a first portion extending below the knee and a second portion extending above the knee. The sleeve is formed of an elastic material to enable it to be stretched so that it can be located on the leg of the person to encircle the person's calf. The sleeve has a top end, a bottom end, an inner surface, an outer surface, sleeve position holding means, and brace mounting means. The inner surface of the sleeve is resistant to sliding on the skin of the person when the sleeve is in place on the calf.

The sleeve position holding means comprises a strap member having a portion fixedly secured to the sleeve adjacent the top end and an elongated free end portion. The free end portion of the strap is arranged to be wrapped around at least a portion of the sleeve adjacent the top end and to be releasably secured in that position, whereupon the inside diameter of the portion of the sleeve underlying the strap is confined to a diameter which is less than the diameter of the widest portion of the wearer's calf so that the sleeve is precluded from slipping down the calf.

The brace mounting means comprises a member fixedly secured to the sleeve at a predetermined position thereon and arranged to be releasably secured to the first portion of the brace to hold the brace in position with respect to the knee.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 4A is a perspective view of a second embodiment of the sleeve of the subject invention;

FIG. 4B is a view similar to FIG. 4A but showing a third embodiment of the subject invention having an anterior pocket.

FIG. 6 is an enlarged sectional view taken along line 6—6 of FIG. 5.

DETAILED DESCRIPTION OF THE PREFERRED EMBODIMENT

Figure 1:
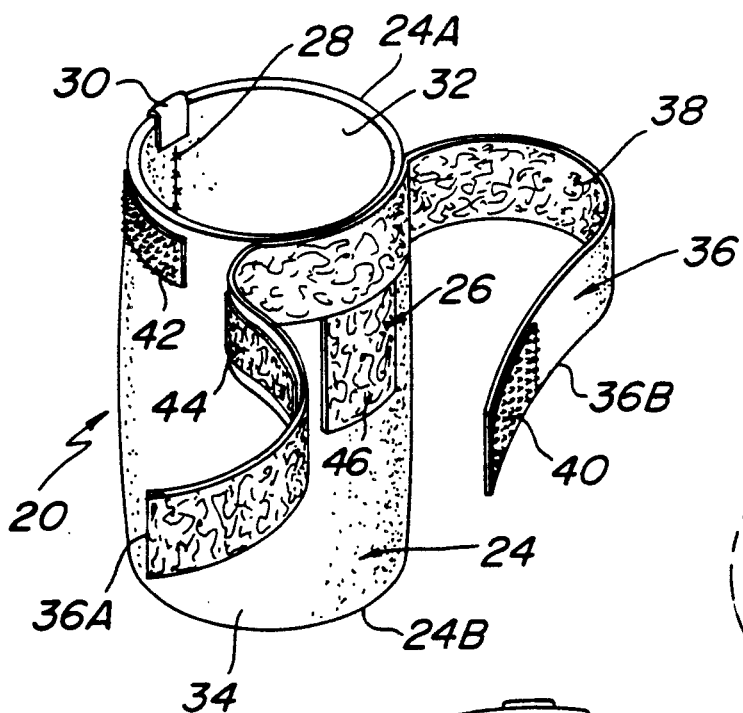
FIG. 1 is a perspective view of one embodiment of the sleeve of the subject invention.

Referring now in detail to the various figures of the drawing wherein like reference characters refer to like parts, there is shown at 20 in FIG. 1 a sleeve constructed in accordance with the subject invention for supporting an orthopedic knee brace 22 (FIGS. 2 and 3) on the knee of a person (not shown) to prevent the brace from slipping down. All of the sleeves of this invention basically comprise a tubular body portion 24 arranged to be worn on the "belly", i.e., the widest portion, of the calf, as will be described later, and releasable supporting means 26 fixedly mounted on the tubular body portion for receiving a portion of the knee brace to releasably support the knee brace thereon.

The releasable supporting means 26 may take various configurations, depending upon the construction of the knee brace 22 to be supported by the sleeve. In the embodiments of the invention shown herein several prior art types of knee braces are shown supported by the sleeves. Those braces are ones of the previously identified prior art braces sold by Pro Orthopedic Devices, Inc., and are merely exemplary. Thus, any other conventional knee brace may be used with the sleeve of this invention by properly configuring the support means on the sleeve to hold the selected brace.

Figure 3A:
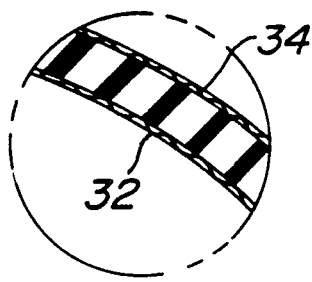
FIG. 3A is an enlarged sectional view of the portion of the sleeve shown within the area bounded by the circle 3A in FIG. 3.
Figure 3:
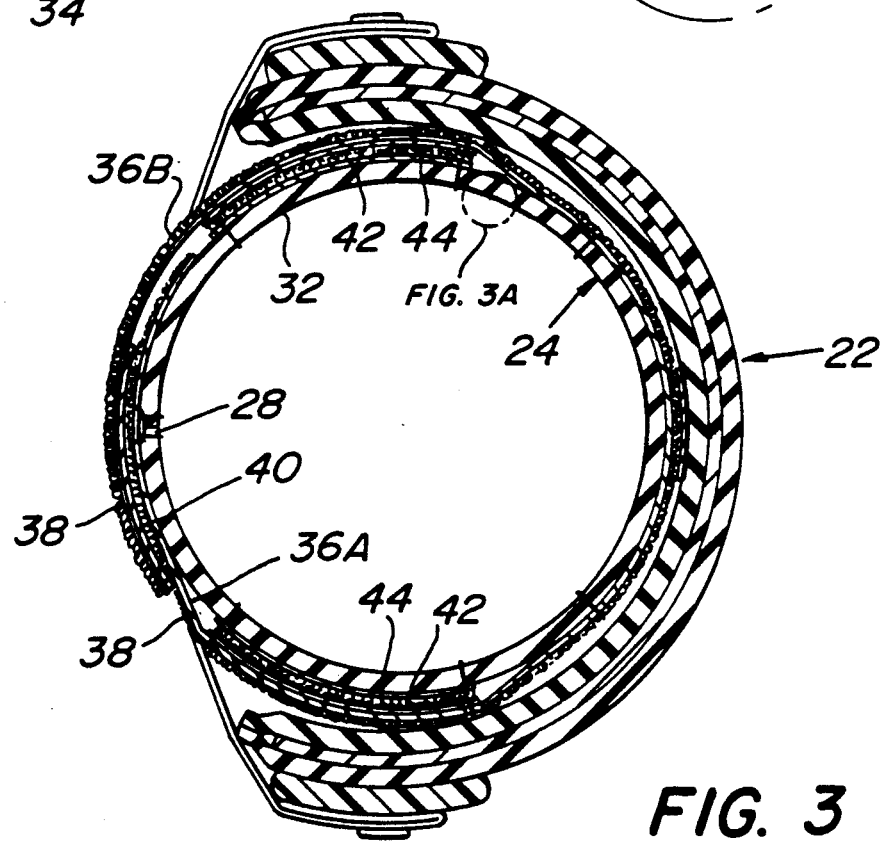
FIG. 3 is an enlarged sectional view taken along line 3—3 of FIG. 2.
Figure 2:
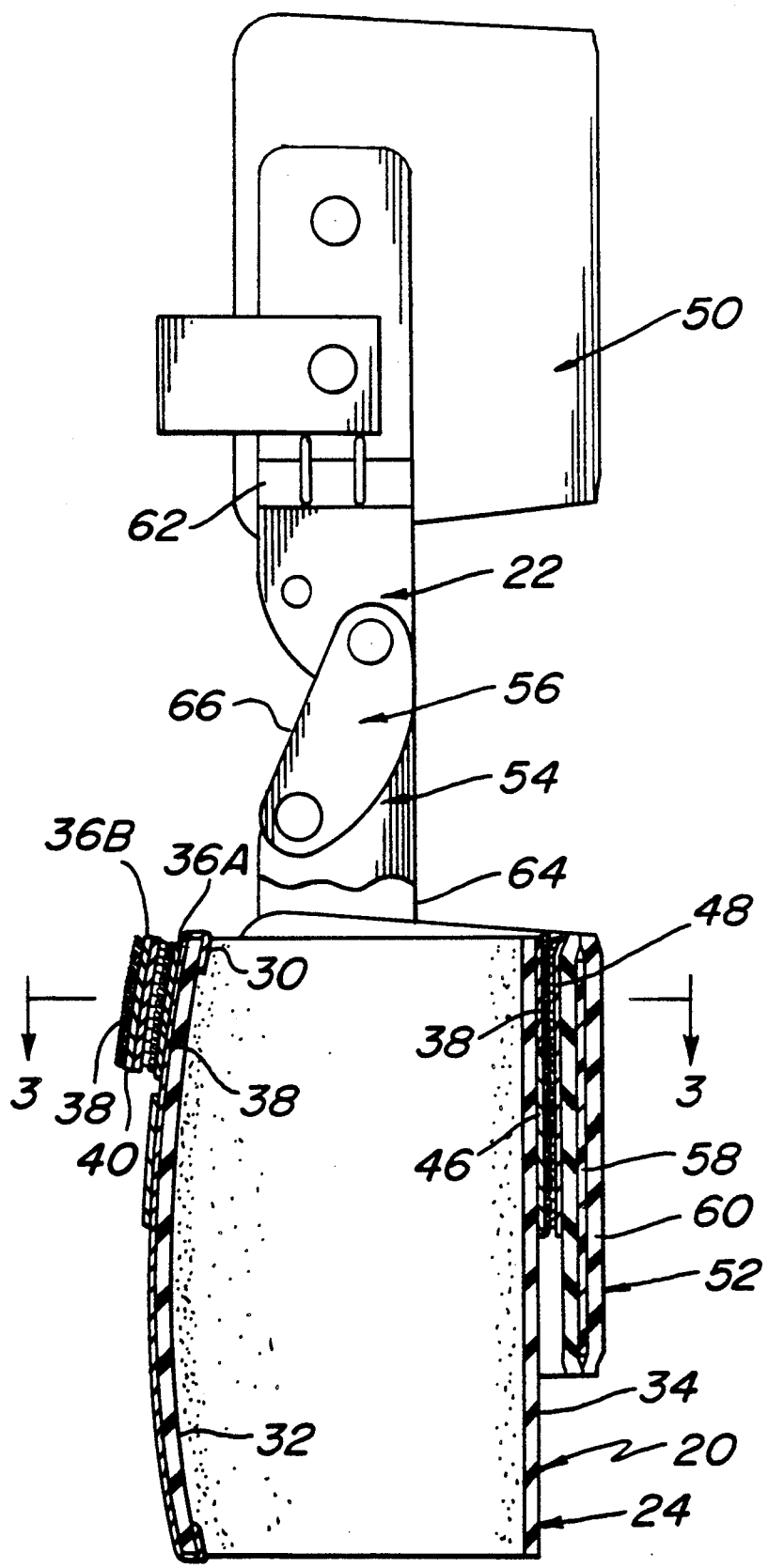
FIG. 2 is an enlarged side elevational view, partially in section, showing the sleeve of FIG. 1 supporting a prior art knee brace.

Referring now to FIGS. 1-3, the first embodiment of the sleeve 20 of this invention will now be described. As can be seen that sleeve comprises a tubular body 24 formed of a web of any suitable flexible and resilient material, e.g., neoprene rubber. In the embodiments shown herein the body 24 includes a vertically extending posterior seam 28 which is sewn and covered by a strip 30 of any suitable flexible material. The body 24 is sized and configured to enable it to be slipped over the wearer's calf with the top end 24A of the sleeve being located immediately below the knee and with the bottom end 24B located closely adjacent the lower extremity of the calf, and once in position to tightly encircle the calf with the inner surface 32 of the sleeve frictionally engaging the wearer's skin to hold the sleeve in place thereat.

The inner surface 32 may be formed of a nylon or other material lining or may be bare rubber, depending upon wearer preference. The exterior surface 34 of the sleeve is preferably in the form of a cloth covering in the interests of durability.

In order to ensure that the sleeve 20 stays in place on the belly of the calf the sleeve also includes position holding means 36. Such means preferably comprises an elongated strap member formed of any suitable flexible, non-stretchable material, e.g., nylon, polyester, etc. The strap member 36 is arranged to tightly encircle the outer surface 34 of the sleeve at the top end 24A to anchor the sleeve in place on the belly of the calf once it has been positioned there.

In the preferred embodiments of this invention the strap 36 is fixedly secured to the sleeve so that it cannot be lost or misplaced. In particular, the middle portion of the strap is sewn to the outer surface 34 of the sleeve at the top end 24A at the anterior side. This arrangement produces a pair of free end portions 36A and 36B of the strap, each of which is arranged to be extended in a respective posterior direction about the top end of the sleeve to encircle the top end of the sleeve.

In order to hold the free end portions in place about the sleeve the strap 36 includes releasable securement means hereon. Such means preferably comprises a conventional VELCRO hook and loop fastening system. In particular a strip 38 of the multi-loop component of the VELCRO fastening system is fixedly secured on the outer surface of the strap 36 along the length thereof, while a patch 40 of the cooperating multi-hook component of the VELCRO fastening system is fixedly secured on the inner surface of the strap portion 36B adjacent the free end thereof. Thus, the strap portions may be releasably held encircling the top of the sleeve by extending the strap portion 36A in one direction about its associated top portion of the sleeve, and then extending the strap portion 36B in the opposite direction about its associated top portion of the sleeve and so that its free end overlies the free end of strap portion 36A, whereupon the VELCRO components 38 and 40 engage each other to hold the strap portions in place.

In order to expedite the procedure for encircling the sleeve by the strap portions 36a and 36B while also ensuring that the straps once in encircling position remain as such the sleeve includes additional releasable securement means for the straps. In particular, the sleeve 20 also preferably includes two patches 42 of the multi-hook component of a VELCRO fastening system and two strips 44 of the multi-loop component of that system. One patch 42 is fixedly secured to the outer surface 34 of the sleeve 20 at the top end 24A of the lateral side, while the other patch 42 is located at approximately the diametrically opposed position, i.e., on the outer surface of the sleeve's medial side at the top end thereof. One strip 44 is fixedly secured to the inner surface of the strap portion 36A, while the other strip 44 is fixedly secured to the inner surface of the strap portion 36B. Accordingly, that when the strap portion 36A is extended about the top of the sleeve the strip 44 mounted thereon releasably engages one patch 42 to hold that strap portion in place along the top of the sleeve. By so doing, the user need not hold strap portion 36A in place with his/her hands as he/she wraps the other portion 36B of the strap 36 about the sleeve's top end 24A. The engaging VELCRO components 42 and 44 associated with the strap portion 36B serve as further means to hold that strap in its encircling position on the sleeve.

As will be appreciated by those skilled in the art with the strap 36 encircling the sleeve 20, as described above, the inside diameter of the portion of the sleeve underlying the strap is confined to a diameter which is less than the diameter of the widest portion, i.e., belly, of the wearer's calf so that the sleeve is locked in place and precluded from slipping down the calf.

The releasable supporting means 26 of the sleeve 20 configured for supporting a brace 20 like that shown in FIGS. 2 and 3 basically comprises a patch 46 of one component, e.g., the multi-loop component, of a VEL- CRO fastening system which is fixedly secured to the outer surface 34 of the sleeve 20 on its anterior side. That component is arranged to be releasably secured to a cooperating, e.g., multi-hook, VELCRO component 48 which is fixedly secured to a portion the brace 22 to thus support the brace on the sleeve.

Before describing the releasable supporting means 26 further a brief discussion of the construction of the brace 22 is in order. To that end the brace 22 shown in FIGS. 2 and 3 is constructed in accordance to U.S. Pat. No. 4,715,363 (Detty). Thus the details of its construction will not be reiterated herein. Suffice it to state that the brace 22 basically comprises a generally U-shaped, upper cuff member 50 configured and arranged to be worn on the person's leg at the thigh just above the knee, a generally U-shaped, lower cuff member 52 configured and arranged to be worn on the person's lower leg just below the knee and opposite to the calf, bracing means 54, and hinge means 56.

Each cuff member includes a central core 58 (FIG. 2), formed of a semi-rigid plastic, such as virgin vinyl, and covered on its inside and outside surfaces with a resilient material 60, such as a closed cell foam, or any other suitable non-allergic material. In addition the outer surface of each of the cuff members 50 and 52 is covered by any suitable fabric, such as Lycra nylon.

The cuff members 50 and 52 are interconnected on the medial and lateral sides thereof by the bracing means 54 and the hinge means 56. The bracing means 54 basically comprises a pair of upper brace members 62 fixedly secured to the upper cuff member 50 and a pair of lower brace members 64 fixedly secured to the lower cuff member 52. Each of the upper brace members 62 is connected to a respective one of the lower brace members 64 by a respective polycentric hinge 66 forming a portion of the heretofore identified hinge means 56 to enable the upper brace members and the cuff member 50 connected thereto to pivot with respect to the lower brace members and the cuff member 52 connected thereto.

As can be seen in FIGS. 1—3 the multi-loop VELCRO patch 46 of the releasable supporting means 26 is located immediately below the central portion of the strap 36 on the anterior side of the sleeve. The cooperating VELCRO component 48 comprises an elongated strip which is fixedly secured, e.g., glued, in a vertical orientation on the inner surface of the lower cuff member 52. Accordingly, when the sleeve 20 is in place as described above and the brace 22 positioned on the knee, the multi-hook VELCRO strip which 48 on the cuff member 52 engages the multi-loop VELCRO patch 46 on the sleeve and also engages a portion of the multi-loop VELCRO strip 38. This action holds the brace at the desired position with respect to the wearer's knee. In order to further secure the brace in place on the wearer's leg a relatively wide band (not shown) is wrapped around the upper cuff and associated portion of the wearer's leg, while a similar band is wrapped around the lower cuff and the associated portion of the wearer's leg. Preferably each band is formed of an elastic material having a rubberized inner surface and a nappy outer surface. The nappy outer surface is suitable for engagement by multi-hook VELCRO fasteners to hold the bands in place.

As should be appreciated from the foregoing the non-elastic strap 36 at the top of the sleeve 20 securely anchors the sleeve on the wearer's leg. Since the strap does not stretch it cannot slide down over the large belly of the calf. The resilient nature of the sleeve aids in maintaining its position by causing its inner surface to snugly and frictionally engage the leg. That combined action provides a very secure base for eliminating brace migration (slippage).

Figure 5:
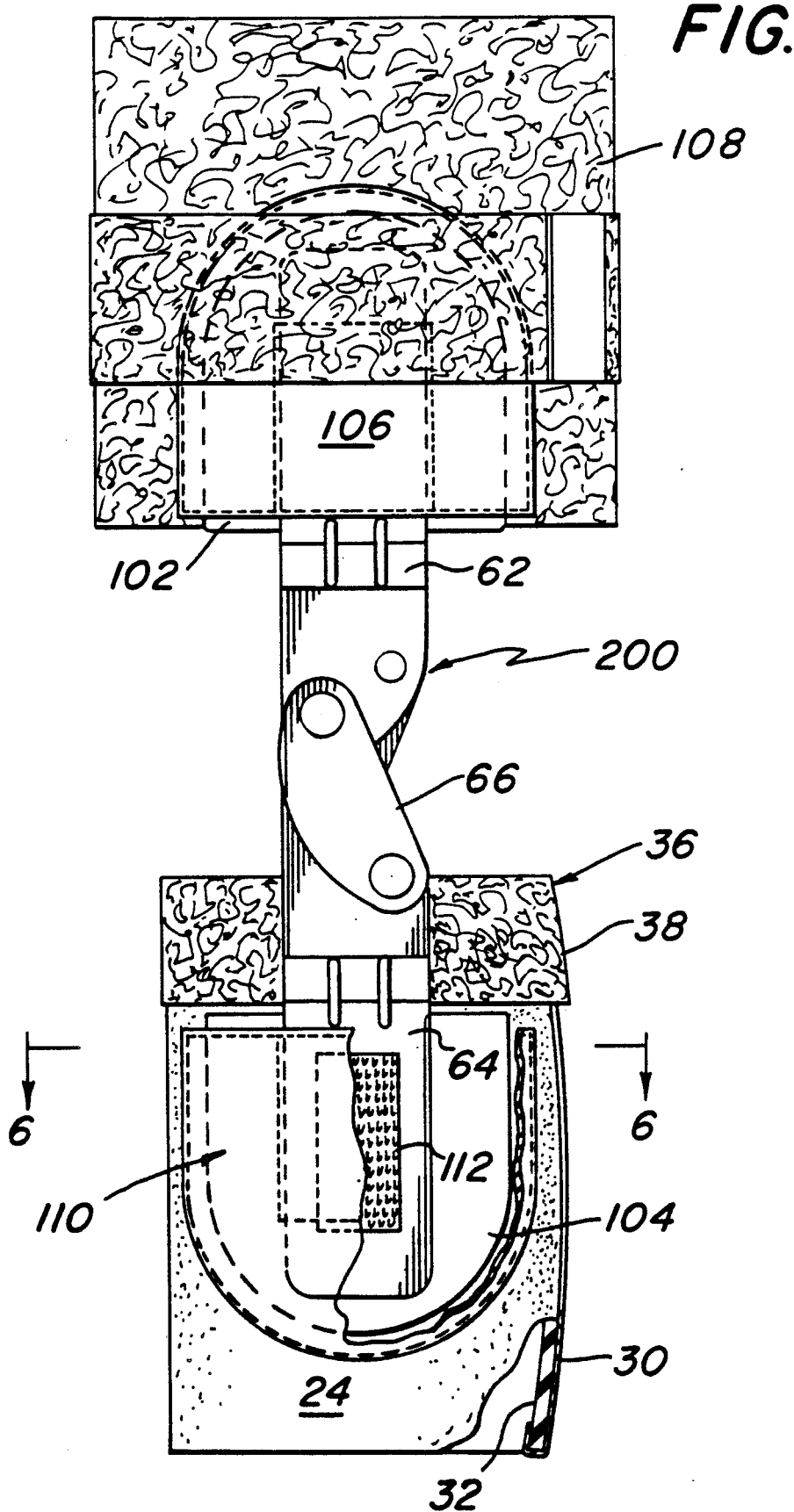
FIG. 5 is an enlarged side elevational view, partially in section, showing the sleeve of FIG. 4 supporting another prior art knee brace.

In FIGS. 4-6 there is shown a second and third embodiments of sleeve constructed in accordance with this invention. Those sleeve is designated by the reference numerals 100 and 300, respectively, and are of basically the same construction as the sleeve 20 described with reference to FIGS. 1-3, except that the means for releasably supporting the brace thereon is different from the means 26 described heretofore to accommodate a different type of brace, namely, a brace 200 (FIG. 5).

Thus, in FIG. 4A there is shown a sleeve 100 having a laterally located pocket (to be described later) for effecting the supporting of the brace 200 thereon, while FIG. 4B shows the sleeve 300 having an anteriorly located pocket (also to be described later) for effecting the support of the brace 22 thereon.

In the interest of brevity common features of the sleeves 20 and 100 will be given the same reference numerals, and the details thereof will not be reiterated. So too, common features of the braces 22 and 200 will be given the same reference numerals, and the details thereof will not be reiterated. The brace 20 is similar in construction to the brace 22 except that brace 200 does not include the cuff members 50 and 52 and does not include pairs of upper and lower brace members 62 and 64. Instead, the brace 100 includes a upper pad 102 constructed similarly to cuff 50, but not of generally U-shape. The shape of the pad 102 is slightly arcuate to conform to the lateral side of the wearer's upper leg. The brace also includes a lower pad 104 of similar construction to the upper pad and configured to conform to the lateral side of the wearer's lower leg. Interconnecting the pads 102 and 104 are a single brace member 62, a single brace member 64, and a single polycentric hinge 66. The upper pad 102 is arranged to be disposed within a pocket 106 in a wide band 108 which encircles the upper leg of the wearer to hold that pad in place on the leg. The lower pad 104 is arranged to be releasably secured to the sleeve 100 to hold it in place on the lower leg.

The releasably supporting means of sleeve 100 for the brace 200 basically comprises a pocket 110 located on the lateral side of the sleeve's tubular body 24. The pocket 110 is configured to receive the lower pad 104 of the brace to releasably secure it therein. In order to ensure that the lower pad stays in position once it is within the pocket 110, releasable fastening means, e.g., VELCRO fasteners, are provided. In particular, a patch 112 of the multi-loop component of a VELCRO fastening system is fixedly secured, e.g., glued, onto the outer surface of the lower pad 104 of the brace, while a cooperating patch 114 of the multi-hook VELCRO component is fixedly secured on the inner surface of the pocket 110. Thus, when the lower pad is disposed within the pocket 110 the VELCRO components 112 and 114 engage each other to hold the pad in place against accidental dislodging.

It must be pointed out at this juncture that the sleeves 20, 100, and 300 described heretofore are merely exemplary of the many configurations the sleeves of this invention may take to accommodate the various types of lower portions of prior art knee braces which are commercially available. Thus, for example, some prior art braces include a lower portion in the form of a rigid member located anteriorly. Such braces may utilize a sleeve like the sleeve 300 so that the anterior pocket may receive the anterior member of the brace. Braces having a laterally located rigid lower member may utilize a sleeve like the sleeve 100 to receive that member.

Alternatively the sleeve may include releasable securement means, such as a VELCRO component located laterally (in lieu of the anteriorly located means 26 of FIGS. 1-3). Moreover, means other than pockets and/or VELCRO fastening can be used to releasably secure the brace onto the sleeve, depending upon the construction and arrangement of the brace.

Without further elaboration, the foregoing will so fully illustrate my invention that others may, by applying current or future knowledge, readily adopt the same for use under various conditions of service.

I claim:

1. A sleeve to hold an orthopedic knee brace in place on the knee of a person, said brace including a first portion extending below said knee and a second portion extending above said knee, said sleeve being a hollow cylindrical member having a closed sidewall comprising a top end, a bottom end, an inner surface, and an outer surface, said sidewall being formed of an elastic material to enable it to be stretched so that it can be located on the leg of the person to encircle the person's calf with the top end of said sidewall being located above the widest portion thereof, said sidewall additionally comprising sleeve position holding means, and brace mounting means, said inner surface of said sidewall being frictionally resistant to sliding on the skin of the person when said sleeve is in place on said calf, whereupon said sleeve stays in place, said sleeve position holding means comprising a strap member formed of a material resistant to stretching, said strap member having a portion fixedly secured to said sidewall adjacent said top end and an elongated free end portion, said free end portion being arranged to be wrapped around at least a portion of said sidewall adjacent said top end and to be releasably secured in that position so that said strap member substantially encircles said sidewall with the inside diameter of the portion of said sidewall underlying said strap member being confined by said strap member to a diameter which is less than the diameter of the widest portion of the wearer's calf, whereupon said sidewall is precluded from stretching and slipping down said calf, said brace mounting means comprising a first member fixedly secured to said sleeve at a predetermined position thereon, said first portion of said brace being arranged to be releasably secured to said first member to hold said brace in position with respect to said knee.

2. The sleeve of claim 1 wherein said free end portion of said strap member is held in position by releasably fastening means.

3. The sleeve of claim 2 wherein said releasable fastening means comprises one component of a two component hook and loop fastening system, said one component being fixedly secured to said free end portion of said strap member, and wherein said sleeve has fixedly secured thereon said other component of said component hook and loop fastening system.

4. The sleeve of claim 1 wherein said sleeve comprises neoprene.

5. The sleeve of claim 4 wherein said inner surface of said sleeve comprises a fabric material.

6. The sleeve of claim 5 wherein said fabric is nylon.

7. The sleeve of claim 1 wherein said sleeve comprises neoprene.

8. The sleeve of claim 7 wherein said inner surface of said sleeve is formed of a fabric material.

9. The sleeve of claim 8 wherein said fabric is nylon.

10. The sleeve of claim 4 wherein said sleeve includes an outer surface formed of a fabric material.

11. The sleeve of claim 10 wherein said fabric is nylon.

12. The sleeve of claim 8 wherein said sleeve includes an outer surface formed of a fabric material.

13. The sleeve of claim 12 wherein said fabric of said inner and outer surface is nylon.

14. The sleeve of claim 1 wherein said brace mounting means comprises one component of a two component hook and loop fastening system, said one component being fixedly secured to said sleeve on the outer surface thereof, and wherein said first portion of said brace has fixedly secured thereon said other component of said two component hook and loop fastening system.

15. The sleeve of claim 14 wherein said one component is mounted on an anterior portion of said sleeve.

16. The sleeve of claim 14 wherein said one component is mounted on a lateral portion of said sleeve.

17. The sleeve of claim 3 wherein said brace mounting means comprises one component of a two component hook and loop fastening system, said one component being fixedly secured to said sleeve on the outer surface thereof, and wherein said first portion of said brace has fixedly secured thereon said other component of said two component hook and loop fastening system.

18. The sleeve of claim 17 wherein said one component is mounted on an anterior portion of said sleeve.

19. The sleeve of claim 17 wherein said one component is mounted on a lateral portion of said sleeve.

20. The sleeve of claim 1 wherein said brace mounting means comprises a pocket adapted to receive therein said first portion of said brace.

21. The sleeve of claim 20 wherein said pocket is mounted on an anterior portion of said sleeve.

22. The sleeve of claim 20 wherein said pocket is mounted on a lateral portion of said sleeve.

23. The sleeve of claim 3 wherein said brace mounting means comprises a pocket adapted to receive therein said first portion of said brace.

24. The sleeve of claim 23 wherein said pocket is mounted on an anterior portion of said sleeve.

25. The sleeve of claim 23 wherein said pocket is mounted on a lateral portion of said sleeve.

* * * * *